United States Patent [19]

Rangaswamy

[11] Patent Number: 4,552,557
[45] Date of Patent: Nov. 12, 1985

[54] INFLATABLE UTERINE HEMOSTAT

[76] Inventor: Avvari Rangaswamy, Stevens Hospital, Welch, W. Va. 24801

[21] Appl. No.: 544,059

[22] Filed: Oct. 21, 1983

[51] Int. Cl.$^4$ .................................. 61F 5/00
[52] U.S. Cl. ........................ 604/96; 128/129
[58] Field of Search .................. 128/129–131, 128/325, 344; 604/96–104

[56] References Cited

U.S. PATENT DOCUMENTS

| | | |
|---|---|---|
| Re. 29,207 | 5/1977 | Bolduc et al. . |
| 444,513 | 1/1891 | Wagner ................................ 128/129 |
| 2,122,579 | 7/1938 | Meckstroth . |
| 3,095,871 | 7/1963 | Mann et al. ........................ 128/344 |
| 3,312,215 | 4/1967 | Silber ................................. 128/131 |
| 3,452,749 | 7/1967 | Riedell .............................. 128/129 |
| 3,464,409 | 10/1965 | Murphy . |
| 3,779,241 | 1/1973 | Vennard et al. ................... 128/129 |
| 3,889,685 | 6/1975 | Miller, Jr. et al. ................. 128/344 |
| 3,918,443 | 11/1975 | Vennard . |
| 3,933,152 | 1/1976 | Moulding . |
| 3,933,153 | 1/1976 | Csatary .............................. 128/130 |
| 3,933,153 | 1/1976 | Csatary et al. . |
| 3,934,580 | 1/1976 | Cournout . |
| 3,994,291 | 11/1976 | Salmasian . |
| 4,137,922 | 2/1979 | Leininger et al. ................. 128/344 |
| 4,291,687 | 9/1981 | Sinnreich ........................... 128/129 |

FOREIGN PATENT DOCUMENTS

| | | | |
|---|---|---|---|
| 1150121 | 7/1983 | Canada .............................. 128/129 |
| 0884398 | 8/1953 | Fed. Rep. of Germany ...... 604/330 |

Primary Examiner—Stephen C. Pellegrino
Assistant Examiner—Karen Kaechele
Attorney, Agent, or Firm—Memel, Jacobs, Pierno and Gersch, Inc.

[57] ABSTRACT

An inflatable intrauterine device to control uterine bleeding, which can also be adapted to permit drainage or aspiration of accumulated blood or mucosal debris from the uterine cavity, is provided.

6 Claims, 5 Drawing Figures

INFLATABLE UTERINE HEMOSTAT

FIELD OF THE INVENTION

This invention relates to an inflatable medical device designed for intrauterine insertion to control uterine bleeding.

BACKGROUND OF THE INVENTION

Uterine bleeding is a commonly encountered clinical condition attributable to a variety of causes, including post-partum hemorrhages following childbirth, post-operative hemorrhages following procedures such as dilation and curettage, and dysfunctional uterine bleeding. Severe uterine bleeding resulting from conditions other than those of the normal menstrual cycle can be a serious problem. For example, about 500 ml. or more of blood is lost in 50% of all childbirths. It can lead to exsanguination, the possibility of peritoneal irritation or infection and other dangerous situations. Hemorrhage is, in fact, one of the major causes of maternal mortality. In one study, maternal death was attributed to hemmorhage in 30% of all maternal deaths. Accordingly, it is desirable to control such bleeding, if possible, at its onset.

Among the various intrauterine devices described in the prior art are those disclosed in U.S. Pat. Nos. 3,933,152, issued Jan. 20, 1976 to Moulding; 3,933,153, issued Jan. 20, 1976 to Csatary et al; 3,994,291, issued Nov. 30, 1976 to Salmasian; 3,918,443, issued Nov. 11, 1975 to Vennard and 3,464,409, issued Oct. 21, 1965 to Murphy. Each of these patents discloses inflatable intrauterine devices which conform to the shape of the uterus.

U.S. Pat. No. Re. 29,207, reissued May 10, 1977 to Bolduc et al. and U.S. Pat. No. 3,934,580, issued Jan. 27, 1976 to Cournout, disclose intrauterine devices capable of dispensing materials into the uterus or fallopian tubes.

None of the aforementioned patents disclose the use of any device to withdraw materials from the uterine cavity. Nor are the devices disclosed designed for or useful for controlling uterine bleeding.

U.S. Pat. No. 2,122,579, issued July 15, 1938 to Meckstroth, discloses an intrauterine device having a semi-rigid non-inflatable head which conforms to the shape of the uterus and an insertion member which acts as a capillary draw. Meckstroth discloses that the purpose of his device is to remove debris from the uterus to relieve amenorrhea and dysmenorrhea. However, no mention is made in the Meckstroth patent of the use of this or any other device to exert pressure on the uterine walls or to control uterine bleeding in any manner.

BRIEF DESCRIPTION OF THE INVENTION

This invention relates to an inflatable medical device capable of being easily inserted into the uterine cavity, and capable of controlling uterine bleeding once inserted and inflated.

This inflatable device may also be adapted to permit accumulated blood or mucosal debris present in the uterus to be drained or aspirated from the uterine cavity.

DETAILED DESCRIPTION OF THE INVENTION

Since the uterus is an organ composed of smooth muscle and therefore susceptible to damage from a rigid intrauterine device, a preferred embodiment of the present invention comprises an inflatable portion made of a soft, pliable material such as rubber (latex rubber being preferred), pliable polymeric sheets or relatively heavy gauge films, animal gut or similar materials. Preferably, some or all of the material comprising this inflatable portion will be radioopaque. Radioopaque materials may be used to form the inflatable portion, or may be incorporated into all or selected areas of the inflatable portion. Radioopacity enables easy location of the inflated portion by X-rays and serves as a means for determining the size and shape of the uterus. Any suitable means of imparting radioopacity to the inflatable portion of the device which will not detract from its pliability may be used, including radioopaque particulate fillers, filaments or the like.

Insertion and proper positioning of the device within the uterine cavity is facilitated by an insertion means, which can be a flexible, semirigid stem or guide, or the like, which is attached to the inflatable portion of the device and surrounded by it. This insertion means can be hollow or solid, and can be made of any suitable material that will not damage the inflatable portion of the device, such as rubber, especially latex rubber, semi-rigid polymeric materials, and the like.

Once the device is inserted and properly positioned in the uterus, its inflatable portion is inflated through a tubular inflation channel, made of any relatively flexible material such as rubber, polymeric materials, and the like, connected to and in communication with the interior of the inflatable portion, using any suitable means, e.g., a fluid such as water, saline solution, air or any other inflating liquid or gas. If a liquid is used to inflate the inflatable portion of the device, it will preferably be of a viscosity such that it will not be difficult to infuse it into or withdraw it from the device. The inflation channel contains proximally located pores through which the inflatable portion can be inflated and deflated once the device has been inserted into the uterus, and will also be adapted at its lower or distal end by means which permit it to be sealed once the inflatable portion has been inflated and to be unsealed to permit the inflating means, e.g., air or other inflating gas, or a liquid such as water, to be bled from the interior of the inflatable portion of the device. The inflation channel can, for example, be provided with a one-way valve at or near its distal end, through which any suitable means for inflating or deflating the inflatable portion of the device—a hypodermic syringe, a hose or tube connected to a fluid source such as an air pump, etc.—can be inserted. Alternatively, a two way valve, a clamp, plug or stopper, or any other suitable means can be used to seal and unseal the distal end of the inflation channel.

The shape of the fully inflated inflatable portion of the device will generally conform as closely as possible to the shape of the interior of the uterus. For example, the inflatable portion of the device will be generally pear shaped when the device is constructed for insertion into the typical human uterus, and will have a width at its upper or proximal end typically, although not necessarily, of about two inches and a width at its lower or distal end, again typically, although not necessarily, of about one half inch. In such a device the length of the insertion means will be typically, although not necessarily, about 2½ inches, exclusive of the inflation channel to which it is connected. These and other dimensions of the device can, of course, be varied to permit the inflatable portion as well as the remainder of the device to conform to and be insertable into human and other mammalian uteruses of any size and shape.

The uterine cavity typically measures approximately 6–8 cm in nulliparous women and approximately 9–10 cm in multiparous women, and the inflatable portion of a device incorporating the present invention configured for use in the human uterus will typically, although not necessarily, have these dimensions when inflated.

The pear shaped configuration of the inflatable portion of a device constructed in accordance with the present invention for use in the typical human uterus permits it to align, once inflated, with the configuration of the uterine interior. As is known, the endometrium is relatively thinner after menstruation (typically, it will be about 0.5 mm thick at this time) and relatively thicker during its proliferative phase (after ovulation and during pregnancy, when it will be about 5 mm thick). This pear shaped configuration of the inventive device, together with the provision of a sheet or film of smooth, pliable material used to form the inflatable portion having a thickness sufficient to exert pressure on the uterine wall, e.g., in the case of a rubber or rubber latex inflatable portion a thickness ranging from about 0.025 mm to about 2 mm, and preferably from about 0.25 mm to about 1 mm, permits the inflatable portion to expand and contract with the uterus while exerting sufficient pressure on uterine blood vessels to curtail bleeding.

The inflatable portion of a device constructed in accordance with the present invention for use in the typical human uterus will generally be inflated to a pressure of from about 40 mm of mercury to about 120 mm of mercury, and preferably to a pressure of from about 60 mm of mercury to about 100 mm of mercury. Any suitable means, e.g., a pressure gauge connected to the inflation channel at its lower or distal end above the means used to seal the inflation channel, can be used to indicate and thus control the extent to which the inflatable portion is inflated. As is known, the pressure gradient in the uterine cavity decreases from above downwards during labor and other situations involving contractions of the uterus.

In a preferred embodiment of the invention twin apical projections, typically although not necessarily of a diameter of about 0.5 cm. when the device is constructed for use in the typical human uterus, designed to conform to and block the entrances to the fallopian tubes, will be appropriately disposed on the inflatable portion of the device at its upper or proximal end. These projections prevent leakage of uterine blood or mucosal debris into the peritoneal area and, as a consequence, help prevent peritoneal irritation or infection.

In yet another and optional embodiment of the present invention, accumulated blood or mucosal debris present in the uterus can be removed, if desired, from the uterine cavity by providing a drainage system comprising a second tubular channel, separate from the inflation channel and attached to the outer surface of the wall of the inflatable portion. This second or drainage channel, which can also be fabricated of rubber, especially latex rubber, polymeric materials and the like, will contain pores or openings at its upper or proximal end, at and above the level of the internal os, through which blood and debris can drain into the second channel and thence out its lower or distal end. Suction may be applied to the lower or distal end to aspirate blood and debris, using any suitable vacuum-producing means, e.g., a suction pump.

Blood and debris can be drained or aspirated through the second channel with the inflatable portion of the device in an inflated or deflated state. Thus, for example, the inflatable portion, once positioned in the uterine cavity and inflated, can be deflated while in place if it becomes difficult to aspirate blood and debris while the inflatable portion is inflated, the blood and debris aspirated by means of the second, separate tubular channel, and the inflatable portion then reinflated by means of the first tubular channel to reexert adequate pressure on the uterine wall.

To insure that the pores or openings in the upper end of the second channel and the second channel itself do not collapse when suction is applied to the second channel while the inflatable portion of the device is in place in an inflated state in the uterine cavity, the walls of the pores and, if desired, the walls of the second channel itself may be reinforced with extra thicknesses of rubber, latex rubber, polymeric material or the like. Also, if desired, crisscrossing channels, suitably reinforced if desired, may be incorporated to communicate between the pores and from the pores to the second channel to facilitate further the drainage of blood and debris.

The diameters of the inflation and drainage channels, taken together, can range from about 3 to about 5 mm in a small device, from about 6 to about 8 mm in a medium sized device and from about 8 to about 10 mm in a large device intended for use in the human uterus. If medium or large devices are employed, and if the cervix is not already dilated, dilation of the cervix by known means may be necessary prior to inserting the device.

DESCRIPTION OF THE ILLUSTRATED EMBODIMENTS

Figure 4:
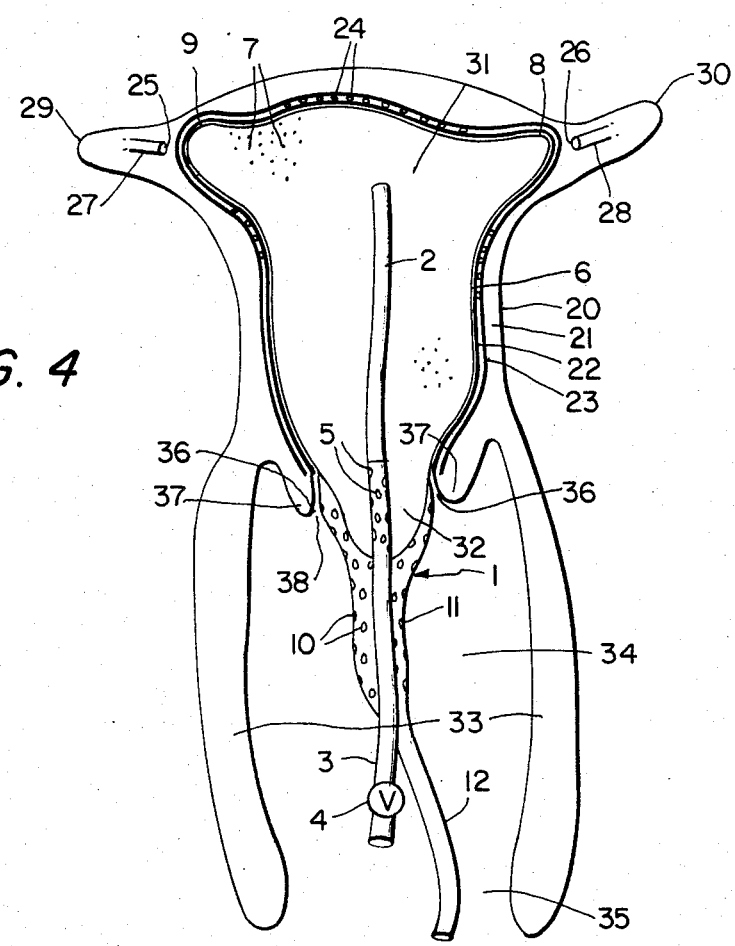
FIG. 4 is a cross sectional front view of an inflated device embodying the present invention illustrating the device in place in the human uterus.

Referring first to FIG. 4, it can be seen that the uterus 20 consists of two layers in addition to the thick muscular layer 21, an outer mucosal layer 22 and an inner muscularis mucosal layer 23 underlying the mucosal layer 22 and containing numerous blood vessels 24. The uterus 20 also contains openings 25 and 26 from the aqueducts 27 and 28 of the fallopian tubes 29 and 30 located in the upper portion of the uterine cavity 31. Generally, the entire uterine cavity is flattened from front to back and triangular in shape from side to side. The lower part 32 of the uterus 20 is integral with an elongate vagina 33. The vagina 33 has a vaginal cavity 34 having an opening or entrance 35. The opposite end 36 of the vaginal cavity 34 is in communication with the cervix 37, having a cervical opening 38 providing a passage from the vaginal cavity 34 into the uterine cavity 31.

A device 1 embodying the present invention has an insertion means in the form of a semirigid flexible rubber stem 2 which facilitates insertion of the device 1 through the cervical opening 38 from the vaginal cavity 34 into the uterine cavity 31.

Figure 1:
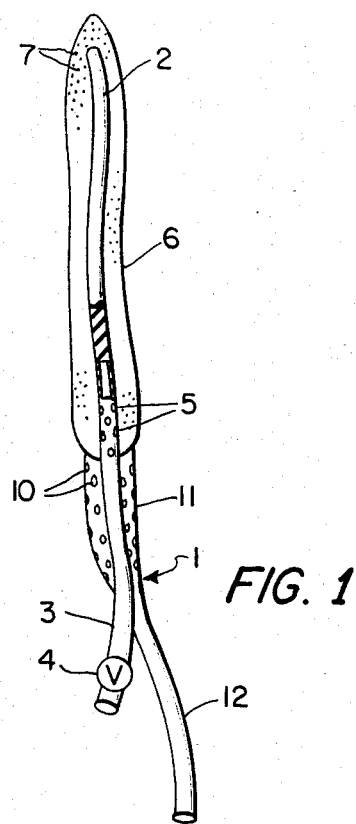
FIG. 1 is a cross sectional view of a device embodying the present invention in an uninflated state, illustrating, among other features, the insertion means, a rubber stem or guide portion used to position the device in the uterus.

Once inserted, the device 1 is inflated through a channel 3 having a seal 4 using any appropriate inflating means such as air or other inflating gas, or a liquid such as water, which passes through the pores 5 to inflate fully the inflatable portion 6 of the device 1. The wall of the inflatable portion 6 can contain radioopaque elements, such as the radioopaque particles 7 illustrated in FIG. 1, which permit the inflatable portion 6 to be easily located by means of X-rays to insure that the device 1 is properly positioned.

Figure 3:
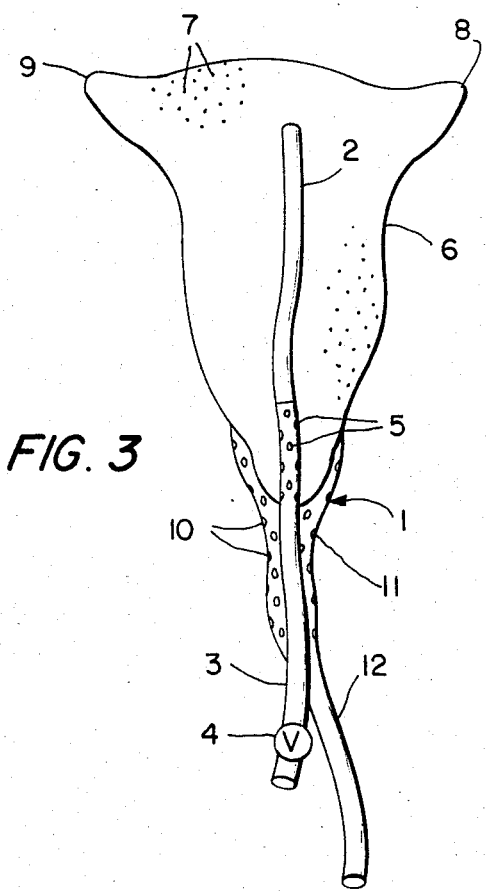
FIG. 3 is a cross sectional front view of an inflated device embodying the present invention, illustrating, among other features, the conformation of the inflatable portion of the device to the side to side triangular shape of the interior of the human uterus.

The inflatable portion 6 of the device 1 is comprised of a resilient pliable material of a sufficient thickness to exert pressure, when fully inflated, against both the uterine mucosal layer 22 and the uterine muscularis mucosal layer 23. Thus, pressure is exerted against the blood vessels 24 in the muscularis mucosal layer 23 thereby constricting these vessels and stopping uterine bleeding. As illustrated in FIGS. 3 and 4, the inflated device 1 conforms to the shape of the uterine cavity and is thus able to exert pressure against all sections of the inner wall of the uterus 20. The inflatable portion 6 of the device 1 should, when inserted, pass beyond the cervix 37 into the uterine cavity 31, since any severe dilation of the cervix 37 by inflation of the inflatable portion 6 of the device 1 therein could cause moderate to severe pain.

As illustrated in FIGS. 3 and 4, the device can also have twin apical projections 8 and 9 which conform to and block the openings 25 and 26 of the aqueducts 27 and 28 of the fallopian tubes 29 and 30. This optional blocking feature prevents any uterine blood or debris from entering the peritoneal area. Any uterine blood or debris which has accumulated before bleeding has been stopped can be aspirated through the pores 10 located on the device 1 at its entrance to the lower part of the uterine cavity 32. These pores 10 are part of a drainage system 11 culminating in a channel 12 separate from the channel 3 used to inflate the device 1.

Figure 2:
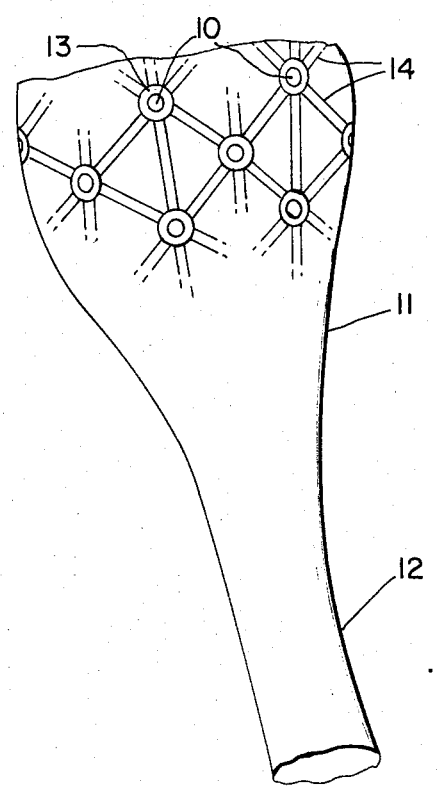
FIG. 2 is an enlarged cross sectional view of the wall of the optional drainage system portion of a device embodying the present invention, illustrating, among other features, pores or openings with reinforced walls and crisscrossing channels communicating between the pores and from them to a drainage channel to facilitate drainage of blood and debris from the uterine cavity.

As illustrated in FIG. 2, the pores 10 in the drainage system 11 can have reinforced walls 13 and crisscrossing channels 14 communicating between the pores 10 and from them to the drainage channel 12. The walls of the drainage system 11 including, of course, those of the drainage channel 12, can likewise be reinforced.

Figure 5:
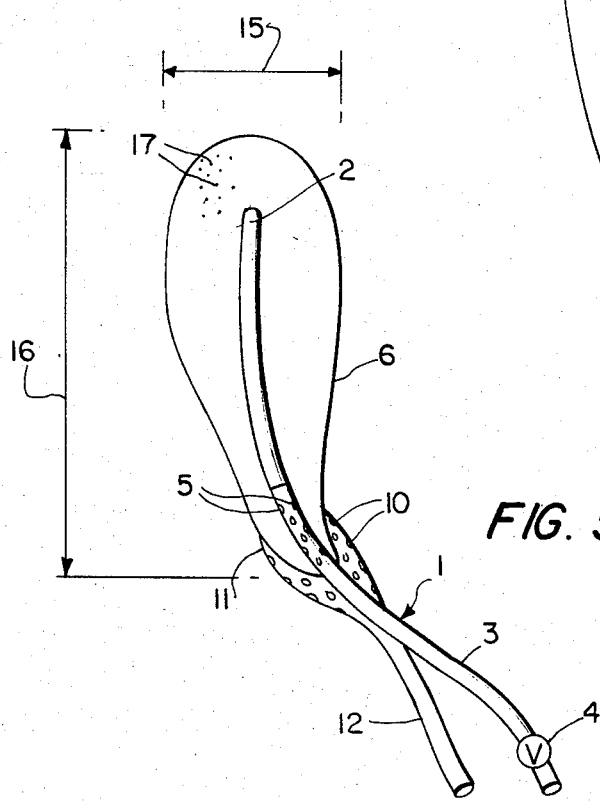
FIG. 5 is a cross sectional side view of an inflated device embodying the present invention, illustrating the conformation of the inflatable portion of the device to the flattened front to back shape of the interior of the human uterus.

FIG. 5 illustrates the fact that the inflatable portion 6 of the device 1, when inflated, is relatively flatter from front to back than from top to bottom, i.e., the distance across line 15—15 is less than the distance across line 16—16, in conformity with the flattened (from front to back) shape of the uterine cavity.

While a preferred embodiment of the intrauterine device of the present invention has been described above, it is obvious that changes in structure and method can be made by those skilled in the art, including changes of size, shape and materials of construction to adapt the device for use not only in different size human uteruses but also for veterinary medical use in other mammalian uteruses, such as those of cows, sheep, mares and other valuable animals, without departing from the spirit of the invention as defined in the appended claims.

I claim:

1. An inflatable uterine device to control uterine bleeding comprising:
   (1) an insertion means which facilitates insertion of the device into the uterus,
   (2) an inflatable portion attached to and surrounding said insertion means which, when inflated, substantially conforms to the shape of the uterus, said inflatable portion having disposed thereon at its proximal end twin apical projections designed to conform to and block the entrances to the fallopian tubes, the wall of said inflatable portion being of a thickness sufficient to exert pressure on the uterine wall to control uterine bleeding,
   (3) a tubular inflation channel connected to and in communication with the interior of said inflatable portion, said tubular inflation channel containing distally located pores through which said inflatable portion can be inflated and deflated once the device has been inserted into the uterus, said tubular inflation channel being adapted at its distal end by means which permit said tubular inflation channel to be sealed once said inflatable portion has been inflated and unsealed to permit an inflating fluid to be bled from the interior of said inflatable portion, and
   (4) a second tubular channel, separate from said tubular inflation channel and attached to the outer surface of the wall of said inflatable portion, containing in its walls proximally located pores to permit drainage of blood and other uterine debris once the device has been inserted into the uterus.

2. An intrauterine device as described in claim 1 in which all or a portion of said inflatable portion has been rendered radioopaque.

3. An intrauterine device as described in claim 2 in which radioopacity has been provided by means of the inclusion, in said inflatable portion, of radioopaque particles.

4. An intrauterine device as described in claim 2 in which radioopacity has been provided by means of the inclusion, in said inflatable portion, of radioopaque filaments.

5. An intrauterine device as described in claim 1 wherein said means at the distal end of said tubular inflation channel comprise a one way valve.

6. An intrauterine device as described in claim 1 wherein said second tubular channel contains in the walls thereof crisscrossing channels communicating between said proximally located pores and from said pores to the distal end of said second tubular channel.

* * * * *